United States Patent
Richardson et al.

(10) Patent No.: US 6,279,574 B1
(45) Date of Patent: *Aug. 28, 2001

(54) VARIABLE FLOW AND PRESSURE VENTILATION SYSTEM

(75) Inventors: Peter Richardson, Sandy; Jeffrey L. Orth; J. Bert Bunnell, both of Salt Lake City, all of UT (US)

(73) Assignee: Bunnell, Incorporated, Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/206,113

(22) Filed: Dec. 4, 1998

(51) Int. Cl.[7] .................................................. A61M 16/00
(52) U.S. Cl. ................................ 128/204.18; 128/204.17
(58) Field of Search ........................ 128/204.17–204.25, 128/207.14–207.16, 910, 911

(56) References Cited

U.S. PATENT DOCUMENTS

| | | | | |
|---|---|---|---|---|
| 3,577,621 | * | 5/1971 | DeGain ................................ | 29/155 |
| 4,471,773 | | 9/1984 | Bunnell et al. . | |
| 4,481,944 | | 11/1984 | Bunnell . | |
| 4,520,812 | | 6/1985 | Freitag et al. . | |
| 4,538,604 | | 9/1985 | Usry et al. . | |
| 4,565,194 | | 1/1986 | Weerda et al. . | |
| 4,573,462 | | 3/1986 | Baum . | |
| 4,682,010 | * | 7/1987 | Drapeau et al. ..................... | 219/381 |
| 4,723,543 | | 2/1988 | Beran . | |
| 4,815,459 | | 3/1989 | Beran . | |
| 5,014,694 | * | 5/1991 | DeVries ........................... | 128/205.24 |
| 5,181,508 | * | 1/1993 | Poole, Jr. ........................ | 128/203.12 |
| 5,207,220 | | 5/1993 | Long . | |
| 5,239,994 | * | 8/1993 | Atkins ............................ | 128/204.18 |
| 5,284,133 | | 2/1994 | Burns et al. . | |
| 5,287,851 | | 2/1994 | Beran et al. . | |
| 5,309,903 | | 5/1994 | Long . | |
| 5,313,939 | * | 5/1994 | Gonzalez ......................... | 128/207.14 |
| 5,319,540 | * | 6/1994 | Isaza et al. ...................... | 128/204.21 |
| 5,331,995 | * | 7/1994 | Westfall et al. .................. | 128/204.21 |

(List continued on next page.)

FOREIGN PATENT DOCUMENTS

2173274 A * 10/1986 (GB) .............................. 128/204.17
WO 98/07401 2/1998 (WO) .

OTHER PUBLICATIONS

American National Standard for Medical Materiel—Luer Taper Fittings—Performance *American National Standard ANSI/HIMA MD70.1–1983*, pp. 7–16.

Standard Specification for Conical Fittings of 15 mm and 22 mm Sizes[1] *American Society for Testing and Materials*, pp. 1–8.

Standard Specification for Tracheal Tube Connectors *American Society for Testing and Materials*, pp. 1–3.

Jet Ventilator Adaptor Sterile Single Use/Disposable *Portex, Inc.*, 2–page pamphlet.

Primary Examiner—Aaron J. Lewis
Assistant Examiner—Teena Mitchell
(74) *Attorney, Agent, or Firm*—Holme Roberts & Owen LLP (57) ABSTRACT

A ventilation system supplies a gas mixture that is humidified and heated through a proportional valve which is a fail closed and normally closed servo control valve positioned proximate a patient. The proportional valve is operated by a controller that regulates the pressure and the mode (e.g., high frequency, normal respiration, combinations) gas is delivered to the patient through a nozzle connected to the endotracheal tube. The nozzle has an exhaust connected to it and a pressure sensor through a pressure sensing port. The exhaust is a capped corrugated tube that is heated and perforated to allow air to escape, to muffle gas and respiration noises, and to trap moisture.

14 Claims, 6 Drawing Sheets

U.S. PATENT DOCUMENTS

| | | | | |
|---|---|---|---|---|
| 5,357,948 | * | 10/1994 | Eilentropp | 128/204.17 |
| 5,392,768 | | 2/1995 | Johansson et al. | |
| 5,400,778 | * | 3/1995 | Jonson et al. | 128/205.19 |
| 5,423,313 | * | 6/1995 | Olsson et al. | 128/204.21 |
| 5,465,728 | * | 11/1995 | Phillips | 128/204.17 |
| 5,522,871 | * | 6/1996 | Sternlicht | 607/107 |
| 5,546,935 | * | 8/1996 | Champeau | 128/205.23 |
| 5,558,083 | * | 9/1996 | Bathe et al. | 128/203.12 |
| 5,598,838 | * | 2/1997 | Servidio et al. | 128/204.21 |
| 5,605,148 | * | 2/1997 | Jones | 128/205.11 |
| 5,664,562 | * | 9/1997 | Bourdon | 128/204.23 |
| 5,664,563 | * | 9/1997 | Schroeder et al. | 128/204.25 |
| 5,682,877 | * | 11/1997 | Mondry | 128/204.23 |
| 5,720,276 | * | 2/1998 | Kobatake et al. | 128/204.18 |
| 5,752,506 | * | 5/1998 | Richardson | 128/204.18 |
| 5,813,399 | * | 9/1998 | Isaza et al. | 128/204.21 |
| 5,909,731 | * | 6/1999 | O'Mahony et al. | 128/205.24 |
| 5,957,020 | * | 9/1999 | Truemner et al. | 83/304 |
| 5,957,129 | * | 9/1999 | Tham et al. | 128/204.22 |
| 5,958,315 | * | 9/1999 | Fatato et al. | 264/46.6 |
| 6,024,089 | * | 2/2000 | Wallace et al. | 128/204.21 |

* cited by examiner

VARIABLE FLOW AND PRESSURE VENTILATION SYSTEM

BACKGROUND

1. Field of the Invention

This invention relates to ventilation systems for use in supplying breathable gas to a patient and more particularly to a ventilation system that supplies treated gas under variable pressure and in accordance with selected modes.

2. State of the Art

The use of mechanical ventilators to deliver a mixture of oxygen and air to a patient's airway in medical treatment situations including, for example, intensive care facilities is known. Known ventilation devices are configured to deliver large volumes of therapeutic gases under positive pressure at frequencies that generally match the normal inhalation rate of the patient. For example, a volume ventilator may deliver a measured quantity of gas at a fixed rate or in response to patient respiratory effort. Use of large gas volume systems has typically been limited to pediatric and adult patients.

Figure 1:
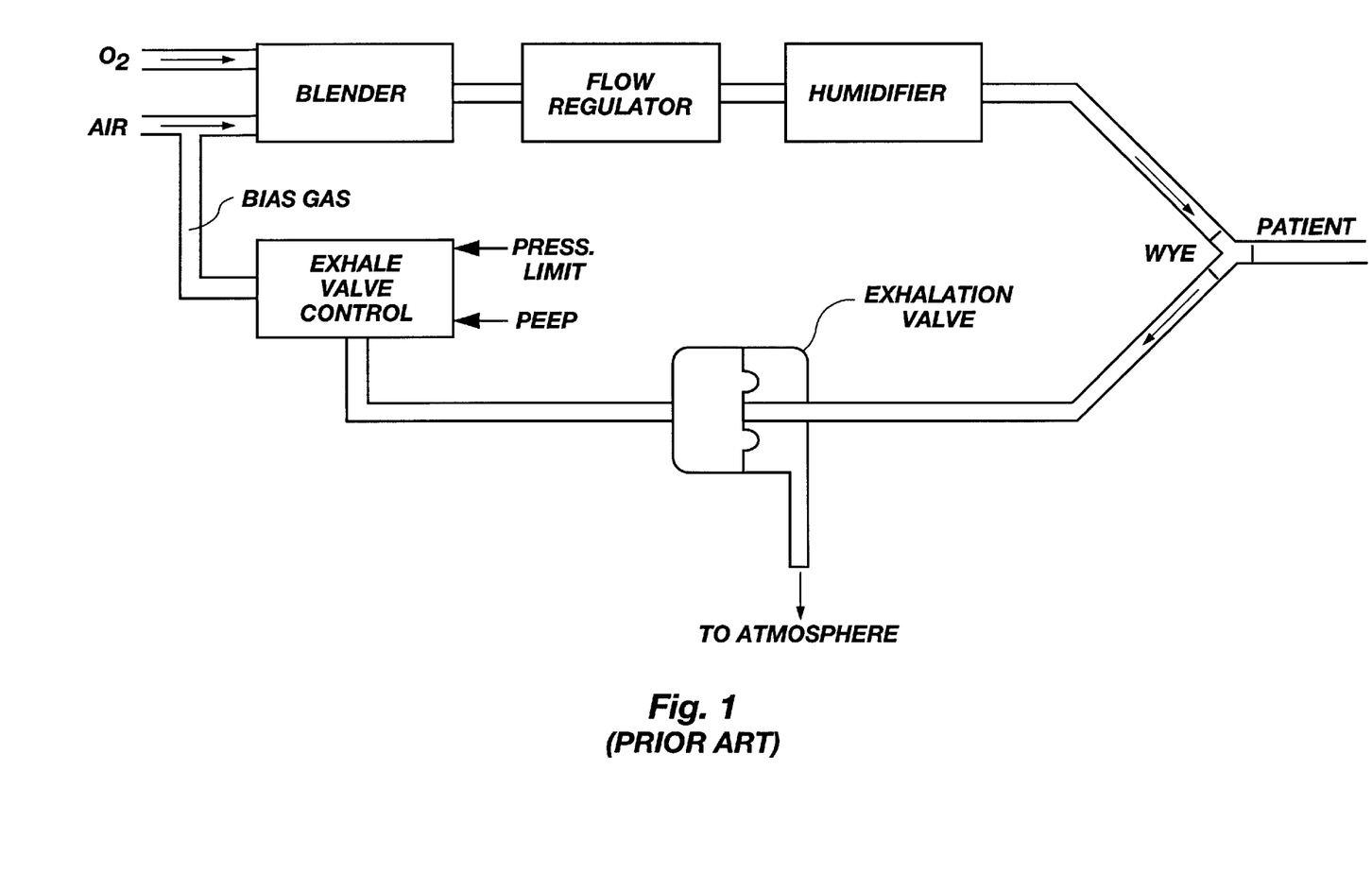
FIG. 1 is a pneumatic diagram of a prior art conventional time-cycled, pressure-limited ventilator.

Another type of ventilator presently in use typically for neonatal and pediatric patients is the time cycled, pressure limited device schematically depicted in FIG. 1. As shown, air and oxygen are blended to a desired ratio by a BLENDER. After passing through a regulator, the mixed gas is heated and humidified in a HUMIDIFIER. The mixed gas then flows from the HUMIDIFIER through the inhalation limb of a patient breathing circuit to a WYE connector. The WYE connector has one end connected to an endotracheal tube for positioning in the trachea of a patient. In turn, the mixed gas is presented to the patient for inhalation through the endotracheal tube. Upon exhalation and during periods where inhalation has been terminated, the mixed gas and exhaust gas then return through the exhalation limb of the breathing circuit to a variable orifice EXHALATION VALVE.

When the EXHALATION VALVE is closed, the flow of the mixed gas into the exhalation limb is blocked or diverted from the exhalation circuit into the endotracheal tube. When the EXHALATION VALVE is open, the gas in the exhalation limb escapes to atmosphere and the patient is free to exhale.

As depicted, the EXHALATION VALVE may be a pneumatically controlled diaphragm valve. Should the pressure in the airway exceed the closing gas pressure of the EXHALATION VALVE, the EXHALATION VALVE would automatically open to relieve the over pressure. Mechanical ventilation may be initiated by varying the control pressure to the EXHALATION VALVE so that the pressure in the airway to the patient varies between a low setting termed the positive end-expiratory pressure (PEEP) to a higher value termed the peak inspiratory pressure (PIP). For the time-cycled pressure-limited ventilator described, the EXHALATION VALVE control pressure is varied from high to low at some fixed rate and the airway pressure automatically limited as described. The bias gas flow to the EXHALE CONTROL VALVE may be adjusted to regulate the EXHALATION VALVE and in turn increase or decrease the PIP pressure, the volume delivered and the flow rate of gas delivered with each inspiratory cycle. Typically the bias gas flow pressure approximates the desired PIP. As a result, the large volume of relatively low pressure gas present in the breathing circuit dictates a relatively slow response time to changes in the control signals to the EXHALATION VALVE from the EXHALE VALVE CONTROL. As a result, systems such as the one illustrated in FIG. 1 typically can not respond to very rapid changes in demand for flow or pressure as in the beginning of inhalation or exhalation. The rapid changes can arise so fast (e.g., a few milliseconds) that the changes are sometimes stated to be "instantaneous." The time lag in supplying sufficient gas or pressure increases the work of spontaneous breathing for the patient when some respiratory therapies are provided which are intended to help limit the work required of the patient to breath but do not in fact assist in limiting the work to the degree desired.

In the treatment of certain respiratory illnesses, it is known to be advantageous to deliver pulses of air and oxygen at frequencies much greater than the normal respiratory rate of the patient. So called high frequency ventilators are designed to deliver small volumes of gas at relatively high rates which typically are greater than one hundred and fifty (150) breaths per minute. Examples of such systems are described in U.S. Pat. Nos. 4,481,944, 4,538,604, and 5,239,994. One known high frequency ventilator uses a jet nozzle to direct gas into the airway of the patient.

Known high frequency ventilator systems do not generally incorporate humidifiers or other components employed in mechanical ventilation. Further, present ventilation systems are bulky and difficult to transport other than on some sort of wheeled cart. Further, such systems do not offer rapid response times along with the ability to select various modes of operation at different pressures and rates.

SUMMARY OF THE INVENTION

It is the object of the present invention to provide a single device that will provide any number of ventilation modes over a range of patient sizes.

It is also an object of the present invention to provide a self contained ventilation system to be portable and in turn facilitate ventilation therapy during patient transport.

It is a further object of the invention to minimize the response time of the system to accommodate synchronous ventilation modes in neonatal and pediatric patients.

It is an additional object of the invention to eliminate positive-pressure bias flow and dead space in the breathing circuit and thereby reduce the work of breathing for the patient undergoing ventilation therapy.

It is yet another object of the invention to measure selected physiologic variables at selected times and to graphically display the physiologic variables including illustrations of the patient's pulmonary function as an aid to the clinician in determining appropriate therapy.

It is a further object of the current invention to provide a system wherein subsequent improvements or modifications to existing treatment protocols may be accomplished via software upgrades.

A ventilation system of the present invention uses a jet of gas directed towards the patient airway to develop a number of controlled gas pressure and flow profiles.

The ventilation system includes a source of both oxygen and air connected to a mixer configured to mix or blend the air and oxygen and to supply one of the air, oxygen or mixture as a breathable gas. The breathable gas is then heated and humidified and supplied to a proportional valve located as near the patient's endotracheal tube as is practical in an effort to minimize the response time of the system to essentially instantaneous changes in demand. The proportional valve is servo-regulated to optimize its performance for any particular demand. The breathable gas is supplied at a relatively high pressure to reduce the response time of the ventilation system. The response time is also regulated and reduced by use of a jet nozzle to deliver breaths to the patient. Further, use of a jet nozzle with a proportional valve positioned close to the patient eliminates the long lengths of large diameter tubing used in conventional breathing circuits and reduces the resistance to flow and delays inherent in these systems.

The electronic microprocessor-based controller includes an interactive display and touch-screen that is desireably configured to act as an input device for establishing operating modes and parameters as well as to graphically display patient status, changes in status over time, pulmonary function curves and protocol management strategies.

The ventilation system is desirably housed in two chassis that are interconnected together. One chassis contains the gas sources, the mixing means and the means to humidify and heat the gas supplied to the proportional valve as well as batteries intended to operate the device during transport or loss of mains power. The other chassis contains the proportional valve and is sized to be small and light weight so it may be placed in proximity to the patient's head.

In a preferred embodiment of a ventilator system designed to accomplish these objectives, a jet nozzle is used to direct gas into one end of an endotracheal tube. The other end of the endotracheal tube is for placement in the airway of a patient. Gas is supplied to the jet nozzle through a proportional valve which varies the flow of the gas to create any desired pressure and flow profile. Control of the proportional valve is accomplished using a microprocessor which responds to the instantaneous pressure and flow measured between the jet nozzle and endotracheal tube as indicative of conditions within the patient airway. Using such a system, it is possible to generate conventional tidal volumes as well as high-frequency breathing waveforms. Locating the proportional valve as close to the patient as is practical (e.g., near the patient's head) minimizes the gas dead-space and improves the system response time. Coincident with the improved response time is the ability to match instantaneous demand for gas flow and pressure and reduce the work of breathing for a patient.

In accordance with the other objectives for the current invention, the system includes a gas mixing and humidification components and a battery power supply for emergency use and for transport. In addition, the system will include sufficient data collection, processing and display capability to present useful clinical information to the clinician.

BRIEF DESCRIPTION OF THE DRAWINGS

In the drawings, which depict what is believed to be the best modes for carrying out the invention.

DESCRIPTION OF THE ILLUSTRATED EMBODIMENT

FIG. 1 schematically shows a conventional time-cycled, pressure-limited ventilator typical of the prior art as hereinbefore described.

Figure 2:
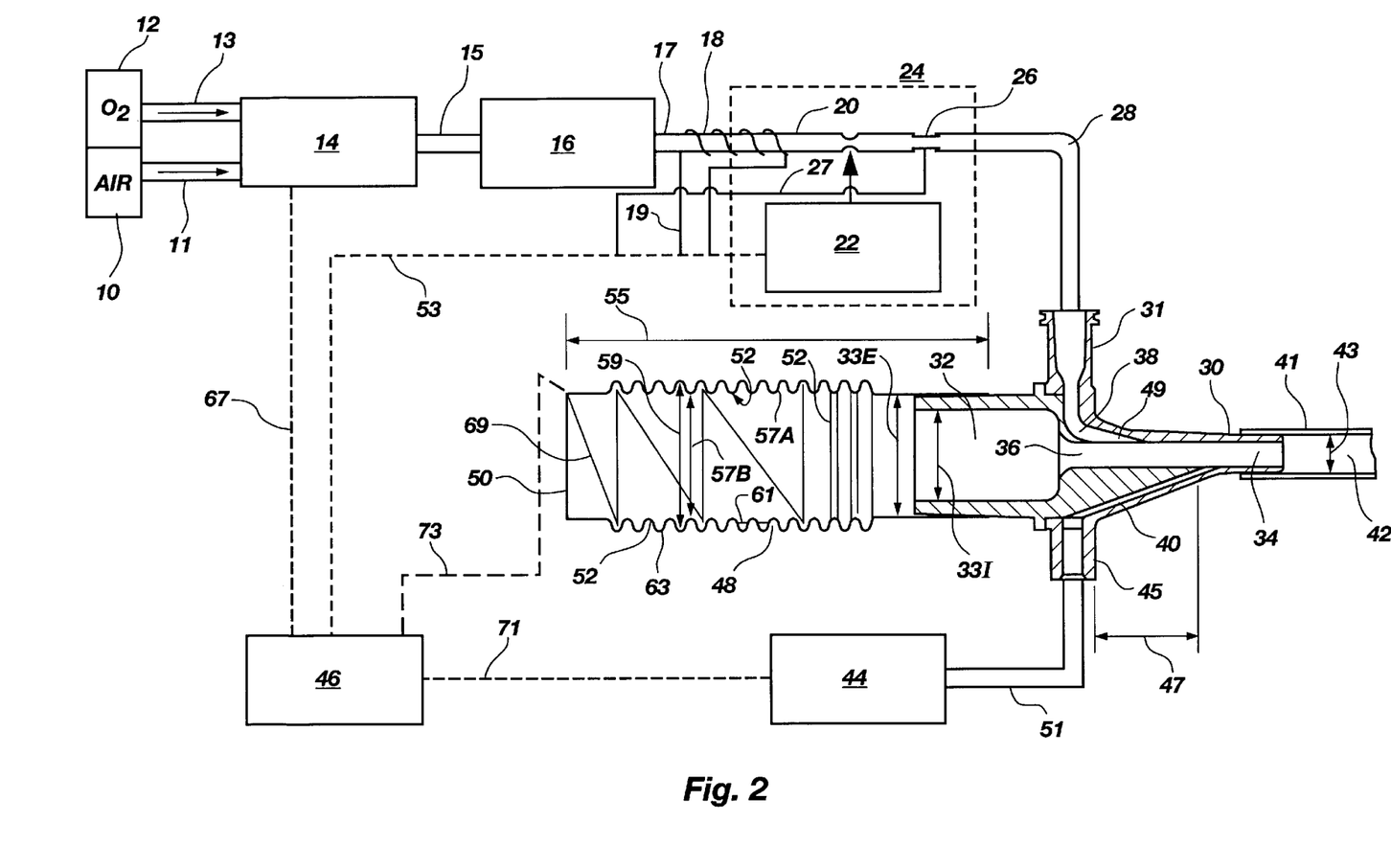
FIG. 2 is a schematic diagram of a ventilator system of the present invention.

FIG. 2 is a simplified schematic diagram of a ventilator system of the present invention. A first source of gas 10 is connected by a conduit 11 to a mixer 14. The mixer 14 has an outlet which supplies breathable gas via conduit 15 to a processing means such as processor 16. The processor 16 may also be referred to as an humidifier and is configured to heat and humidify the breathable gas from the mixer 14. The processor 16 heats the breathable gas to a temperature of approximately 37° C. and raises its humidity to 100% RH after the gas is allowed to expand to a pressure selected by the user.

The processor 16 supplies at its outlet 17 processed gas which flows through a length of delivery tubing 18. The delivery tubing 18 is configured to include a heater wire 19 which is operable to maintain the temperature of the processed gas. As here shown the heater wire 19 is depicted wrapped about the delivery tubing. However, the heater wire may be unitarily formed in the side wall of the delivery tubing 18, disposed in the interior, or otherwise positioned to heat the gas directly or through the sidewall of the delivery tubing 18. The delivery tubing 18 also includes a section of compliant tubing 20 located to extend relative to a proportional valve 22 which is here depicted as a pinch valve. That is, the pinch valve functions to pinch the compliant tubing 20 to restrict flow therethrough or therepast. The proportional valve 22 is contained within a chassis 24 which is itself configured to be placed proximate the patient's head. The proportional valve 22 operates to regulate the pressure and to deliver the processed gas to the nozzle 30 following or in accordance with a selected mode (e.g., high frequency, normal respiration, patient activated, machine activated, and combinations of the same).

If the proportional valve 22 is a solenoid operated pinch valve, it may desirably be spring loaded to exert force compressing the compliant tubing 20 so as to be normally closed. When power is applied to the solenoid of the pinch valve 22, the pinch valve opens generally in proportion to the power applied. That is, the power may be applied by varying the voltage, the current or the energy (kilowatts) supplied to induce a predictable mechanical response in valve movement to regulate and supply a predictable amount of processed gas to flow through.

A second delivery tube 28 connects the compliant tube 20 within the pinch valve 22 to the jet nozzle 30. A small metal sleeve 26 between the compliant tube 20 and the delivery tube 28 is used in conjunction with a temperature sensing device to monitor the temperature of the processed gas within the tubing 28 and to supply a signal reflective of the temperature via conductor 27. That is, the sleeve 26 is thermally conductive so that it reflects the temperature of the processed gas therein.

The second delivery tube 28 is connected to a supply port 31 of the jet nozzle 30. It includes a proximal opening 32 that has interior diameter 33I as well as an exterior diameter 33E. The exterior diameter 33E is sized to match or connect to any suitable tube and may be from about 15 or about 22 mm for connection to standard medical tubing.

The distal end 34 of the jet nozzle 30 is designed to fit the inside lumen 42 of a standard sized endotracheal tube 41 including those which may vary in size from 2.0 to 6.0 mm inside diameter 43 for neonatal and pediatric patients. The jet nozzle 30 also has a central lumen 36 to which the supply port 31 connects through the channel 38. The channel 38 exits into the central lumen 36 at an oblique angle so that gas introduced through this channel 38 is directed towards the central lumen 36 toward the endotracheal tube 41 and the patient's airway. The second port 45 connects to the central lumen 36 of the jet nozzle adapter 30 through the channel 40 at a distance 47 spaced from the opening 49 of the first port 38 and is used to monitor the patient airway pressure.

During inhalation, the pinch valve 22 is opened and gas is directed towards the patient through the jet lumen 38 of the nozzle adapter 30 which is connected to an endotracheal tube 42. The pressure in the patient airway as reflected through the pressure monitoring port 45 of the jet nozzle adapter 30 is measured using a pressure transducer 44 through conduit 51. The measured pressure is compared to a desired pressure and over time the pressures detected are compared to a desired waveform by an electronic control device 46.

The electronic control device varies the power applied to the pinch valve 22 through conductor means 53. That is, conductor means 53 includes a plurality of conductors one or more of which is/are connected to supply power to the pinch valve 22. In addition, the control device 46 may adjust the gas pressure from the mixer 14 into conduit 15 to provide breathable gas at a sufficient pressure to meet the requirements for any particular volume or pressure required for the breath being delivered. That is, a signal is supplied via conductor 67 to operate the mixer and in turn regulate the pressure of the breathable gas. The pressure of the breathable gas will be thereby adjusted so that the pinch valve 22 will operate through a large portion of it's mechanical range to increase the resolution of the system.

During exhalation, the patient simply breaths out through the endotracheal tube 42 and the central lumen 36 of the jet nozzle adapter 30 and the proximal end 32 to atmosphere. Alternately, a length 55 of 15 or 22 mm corrugated tube 48 may be attached to the proximal end 32 of the jet nozzle adapter 30 to direct the exhaled gas away from the patient. This corrugated exhalation tube 48 may include a water trap and a heater wire 69. Alternately, the corrugated exhalation tube 48 may be closed at one end by a cap 50.

The corrugated exhalation tube 48 preferably is formed with a number of small holes 52 provided to allow exhaled gas to escape. By forming a large number of the small holes 52 circumferentially on the innermost surface 57A of the corrugations of the exhalation tube 48, the chance of occlusion by condensate or by bedding materials becomes very slight. The innermost surface 57A has a minor diameter 57B. The corrugations have the minor diameter 57B and a major diameter 59. As shown, water, condensate or other fluids 61 may collect in the channels 63 formed between the innermost surfaces 57A. In turn the water, condensate or other fluids 61 are kept away from the holes 52 formed proximate the interior diameter 57B. The holes 52 also limit or muffle any noise generated by the jet of gas during inhalation.

It can also be seen in FIG. 2 that the pressure transducer 44 is connected by conductors 71 to supply signals to a control 46. The heater wire 69 in the corrugations 48 is also operated by the control 44 via conductor 73.

Figure 3:
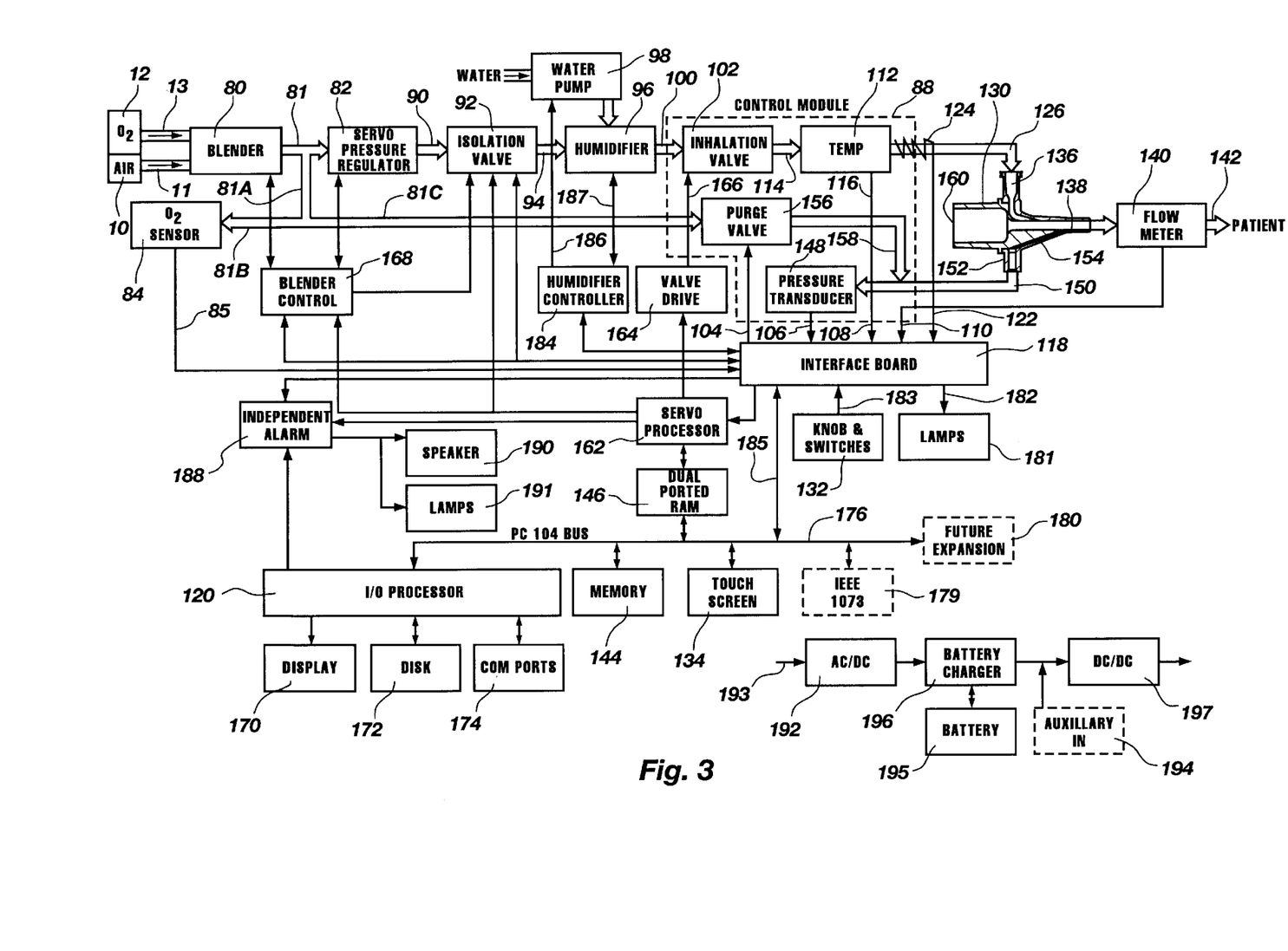
FIG. 3 is a block diagram of a complete ventilator system of the present invention.

FIG. 3 is a block diagram of the entire ventilator system according to the principles of the present invention. As before, a first source of gas is a source of compressed air 10; and a second source of gas is a source of oxygen 12. Each are connected by conduits 11 and 13 respectively to a gas blender 80. The blender 80 functions to mix the gases and produce breathable gas which may be air, oxygen or a mixture of the two. The output of the blender 80 is supplied via a conduit 81 to a pressure regulator 82. The pressure regulator 82 senses the pressure of the breathable gas in the conduit 81 or received from the conduit 81 and operates to supply the breathable gas at its output via conduit 90 at a pressure selected by the user as more fully discussed hereinafter.

Some portion of the breathable gas is available via conduits 81A and 81B to an oxygen sensor 84 which monitors the percentage of oxygen in the breathable gas and sends a signal via conductor 85 to trigger an alarm should the percentage vary significantly (e.g., more than 10%) from the desired value. The breathable gas is also made available to a purge valve 156 within the control module 88 via conduit 81C.

Once breathable gas has been regulated to the desired driving pressure by the servo regulator 82, it passes through conduit 90 to an isolation valve 92. The isolation valve 92 is normally held open during operation but may be closed in an emergency to prevent excessive gas from reaching the patient. In other words, the isolation valve is a servo or electrically operated valve that is electrically operated to open and mechanically operated to a closed position by, for example, a spring. In short, the isolation valve fails closed.

The breathable gas is supplied via conduit 94 to a humidifier 96 which operates to heat and humidify the breathable gas. A water level sense mechanism within the humidifier 96 controls a water pump 98 to keep a constant level of water within a reservoir in the humidifier 96. As the breathable gas pressure may vary between 2 and 25 psig, it is necessary to introduce water into the humidifier 96 under pressure using the water pump 98 rather than a simple gravity feed system as used by conventional, low pressure humidifiers. The humidifier 96 operates comparable to those disclosed in U.S. Pat. No. 4,588,425 the disclosure of which is hereby incorporated by this reference.

From the humidifier 96, the now processed gas travels through a length of delivery tubing 100 to the inhalation valve 102 within the control module 88. The control module 88 is positioned within a small chassis connected to the main body of the ventilator system by a tether containing both electrical conductors such as conductors 104, 106, 108 and 110 and pneumatic lines such as conduit 100. The tether may be from about two to about 10 feet and is preferably about four (4) feet in length. That is the tether is sized so that the control module 88 may be placed in the patient's bed and preferably as close to the patient s head as is practical. The tether may be a tubular sleeve sized to contain the conductors 104–110 and the conduit 100.

Similar to proportional valve 22 of FIG. 2, the proportional valve 102 is a spring loaded pinch valve and is normally closed. When the proportional valve 102 opens, the processed gas flows through to a section of metal tubing which is in intimate contact with a temperature sensing device similar to section 26 of FIG. 2. The temperature sensing assembly 112 is contained within a thermally neutral portion of the patient control module 88 so that the temperature of the tubing 114 reflects the temperature of the gas within the tubing. A temperature signal reflective of the temperature of the processed gas in the tubing 114 is developed by the temperature sensing assembly and sent via conductor 116 to an interface board 118. The temperature signal is processed through the interface board 116 and sent to the humidifier controller 184 which supplies signals back through the interface board 118 to regulate a heating wire 124 connected by conductor means 122. The heating wire is placed in or about the gas delivery tubing 114 or 126. The temperature of the processed gas is detected downstream of the proportional valve 102 so that the processed gas has expanded to the delivery pressure. That is, absent further heating, the processed gas will be at a temperature close to that when it the processed gas is delivered to the patient through the nozzle 130. That is the gas could cool or heat from ambient conditions as it progresses through the tubing 126 and the nozzle 130 into the patient. However, since the amount of the temperature change can be predicted between the temperature at the temperature sensing assembly 112 and the nozzle, a desired temperature for the processed gas can be selected by the user through operation of knobs and switches 132 or touch screen 134.

When the proportional valve 102 opens, processed gas travels through the temperature sensing assembly 112 and through a length of delivery tubing 126 to the inlet port 136 of the nozzle 130. Processed gas is in turn directed into the central channel 138 towards the patient through a flowmeter 140 and then into an endotracheal tube 142. The flowmeter 140 may be of any of the conventional designs including heated wire, venturi or variable orifice or more preferably, transit-time ultrasound. The flow meter 140 may be a separate assembly, or an integral part of the nozzle 130. The flow meter sends a signal reflective of gas flow to the interface board 118 for further transmission to the processor 120 and memory 144 and 146 for storage and processing in accordance with control functions programmed or desired.

The pressure within the nozzle 130 is monitored by a pressure transducer 148 within the patient control module 88 by means of a second port 152 of the nozzle 130 and a short length of tubing 150. The second port 152 is in communication with the central channel 138 through a small sensing channel 154. Should the small sensing channel 154 become occluded by mucous or other fluids as sensed by a deterioration of the pressure signal derived from the pressure transducer 148, the purge valve 156 may be opened briefly to supply breathable gas via conduit 158 into the short length of tubing 150 and the small sensing channel 154 of the nozzle 130. The increased gas pressure within urges any obstructing material into the central channel 138 where it may be removed by suction or urged outwardly through the exhaust port 160 by, for example, the exhalation of the patient. Of course as the short length of tubing 150 and/or the small sensing channel 154 are cleared a stable pressure signal is restored; and the purge valve 156 is thereupon closed. Of course the servo processor 162 may limit the total time the purge valve 156 is open (e.g., 15 milliseconds) and may provide for repeated purge operations until an obstruction is cleared. The servo processor 162 may also send a signal to the interface board or an associated monitor to display an image or generate an audio signal reflecting operation of the purge valve and the condition of the incoming pressure signal from the pressure transducer 118.

Gas delivery to the patient is controlled by a microprocessor which includes the servo processor 162. This component may be a digital processor similar to the Motorola 68000 or the Intel 80×86 family of parts or more preferably, a digital signal processor (DSP) similar to the Analog Devices 2100 or the Texas Instrument 3200 series parts. The servo processor 162 receives the airway pressure signal from the pressure transducer 148 within the patient control module 88 through an appropriate amplification and analog-to-digital converter located on or included as a circuit board portion of the interface board 118. The servo processor 162 uses the pressure signal as a feedback control signal to help generate and regulate a signal supplied to the valve drive 164 to vary the flow through the proportional valve 102. The proportional-valve-control signal generated by the servo processor 162 is converted to a current by the valve drive 164 supplied to the proportional valve 102 by conductor 166. The proportional valve 102 is current rather than voltage driven to reduce the effects of the change in resistance of the valve coil due to temperature change with use.

If the proportional valve 102 is completely open and the pressure and/or flow measured at the patient is not as great as desired, the servo processor 162 may increase the gas pressure for the breathable gas and the processed gas by sending the appropriate commands to the blender controller 168. The servo processor 162 adjusts the pressure as determined by the pressure regulator 82 through the blender controller 168 so that the proportional valve 102 is able to operate through a large portion of it's mechanical range. Increasing the pressure of the processed gas facilitates e control of the pressure and flow waveform of the gas delivered to the patient through the nozzle 130.

A second microprocessor 120 is most preferably a digital microprocessor and operates to communicate with the clinician. The second processor is labeled as the I/O (Input/Output) processor in FIG. 3 to show that its function is to interface with the operator or clinician. The I/O processor 120 is connected to a large, color LCD display 170, a floppy disk drive 172 and a number of serial and parallel communications ports 174 for attachment to other devices. A data bus 176, shown as a PC104 standard, is used to interconnect the I/O processor 120 with a number of other devices including additional memory 144, a touch screen overlay 134 for the LCD display, an IEEE medical information data bus connection 179, the interface board 118, and a block of dual ported random access memory (DPRAM) 146. The touchscreen 134 is preferably of the resistive or infra-red type so that the screen may be sealed against fluid spills and allow the use of instruments or gloved hands for operation. A capacitive or surface wave acoustic design could also be used but is less preferable because it would require the use of a tool to be grasped by the user or require the clinician to remove rubber gloves and thereby create an inconvenience and even increase the risk of contamination of the clinician and/or the touch screen. A modem may be incorporated in order to transmit data to remote locations or other PC104 compatible devices may be added including, but not limited to additional memory or a GPIB interface through a future expansion site 180.

The I/O processor 120 receives commands from the clinician regarding the desired mode of ventilation (e.g., high frequency pulse, normal respiration, combinations of high frequency and normal respiration breath rate), PIP, PEEP, patient initiated operation (upon initiating an inspiration) or a system imposed regimen all through the interactive touch screen 134 and display 170. As an example, should the clinician desire to change the percentage of oxygen delivered to the patient, the oxygen percentage is depicted by an icon on the display. The icon would be touched to simulate the operation of a button via the touch screen 134 or through a rotary knob and switches 132 attached to the interface board 118. The knob can be turned until the desired percentage oxygen was displayed on the display 170.

A similar set of commands can be introduced through the touch screen 134 as well as through the same rotary knob and switches 132 In addition, the I/O processor 120 receives signals reflective of airway pressure and flow information through the interface board 118 and operates to present on the display 170 the resultant waveforms and calculated maximum and minimum values numerically for various parameters such as the PEEP and PIP. Certain commands such as "operate" and "standby" will be implemented using fixed switches which are part of the knob and switches 132 unit. Signals reflective of operation are transmitted to the interface board via conductor 183. Operation of the switches and the knob 132 is reflected by the illumination of appropriate lamps 181 connected by conductor 182 to the interface board 118.

The humidifier 96 temperature settings are controlled by the clinician using commands input through the touch screen 134, rotary knob and switches 132 and I/O processor 120. A signal reflective of the desired temperature setting is generated and supplied via the bus 176 and conductor means 185 for further transmission to a separate humidifier controller circuit 184. The humidifier controller circuit supplies signals via conductor 186 to the water pump to cause water to be supplied to the humidifier 96 and via conductor 187 to control the heater in the humidifier 96 all in accordance with preselected parameters to develop a desired humidity for the processed gas supplied at the output of the humidifier 96.

The DPRAM 146 is accessible by both the I/O processor 120 and the servo processor 162. The additional memory provided by DPRAM 146 is used to transfer information between the two processors regarding the desired mode of ventilation and flow and pressure settings and the actual pressure and flow monitored. The DPRAM 146 also acts as a kind of "fire wall" to isolate the servo processor 162 from software including viruses and the like that may be present in the I/O processor 120. As a result, the operation of the proportional valve 102 to deliver processed gas to the patient is controlled by the software installed in the servo processor 162 at the time of manufacture and may not be corrupted by other software that may be introduced into the I/O processor 120 through for example, the disk drive 172.

Should an error in the performance of any of the functional blocks of the ventilator system be detected by either the servo processor 162, the I/O processor 120, or the blender controller 168, the isolation valve 92 may be closed to protect the patient from excessive gas pressure or volumes. Each of the servo processor 162, the I/O processor 120, or the blender controller 168, the isolation valve 92 may also cause the independent alarm circuit 188 to generate an audible alarm through a speaker 190 and a visual alarm through a number of lamps 191. The alarm lamps 191 are located on the exterior of the enclosure so they are visible from a wide viewing range as an aid in identifying the particular piece of equipment, that may be among many, as having a fault condition.

The various components of the system illustrated in FIG. 3 are supplied with electrical power by conductors that are not shown to simplify illustration. Power is provided either through through a conventional plug or wire input 193 or through an auxiliary direct current (DC) input 194. AC line current input 193 is converted to DC current by an AC/DC converter 192 and used to power a battery charger 196. The battery charger 196 maintains the charge on an integral secondary battery system 195 and provides power to a number of DC to DC converters 197 that in turn provide the requisite voltages to the remainder of the components in the system of FIG. 3. Should the ac power 193 fail or be removed for transport, the battery 195 will automatically be switched in and provide sufficient operating power for a selected period of time related to the size of the battery, the state of charge of the battery, the mode of operation of the system and related factors. Operation for periods in excess of 30 minutes is expected.

In FIG. 3, a variety of other conductors are shown to reflect electrical interconnection of the several components and the transmission of signals therebetween to effect operation of the system. It may also be noted that in FIG. 3, a muffler is not shown attached to the nozzle 130. A muffler such as muffler 48 may be used as desired. Also it should be noted that the gases supplied include oxygen and air. In some applications, other gasses may be added including nitrogen. It should also be noted that in lieu of water supplied by the pump 98, therapeutic liquids could be added.

Alternately, therapeutic substances may be inserted by use of a Y connection in the tubing 126 or in the tubing 100.

Figure 4:
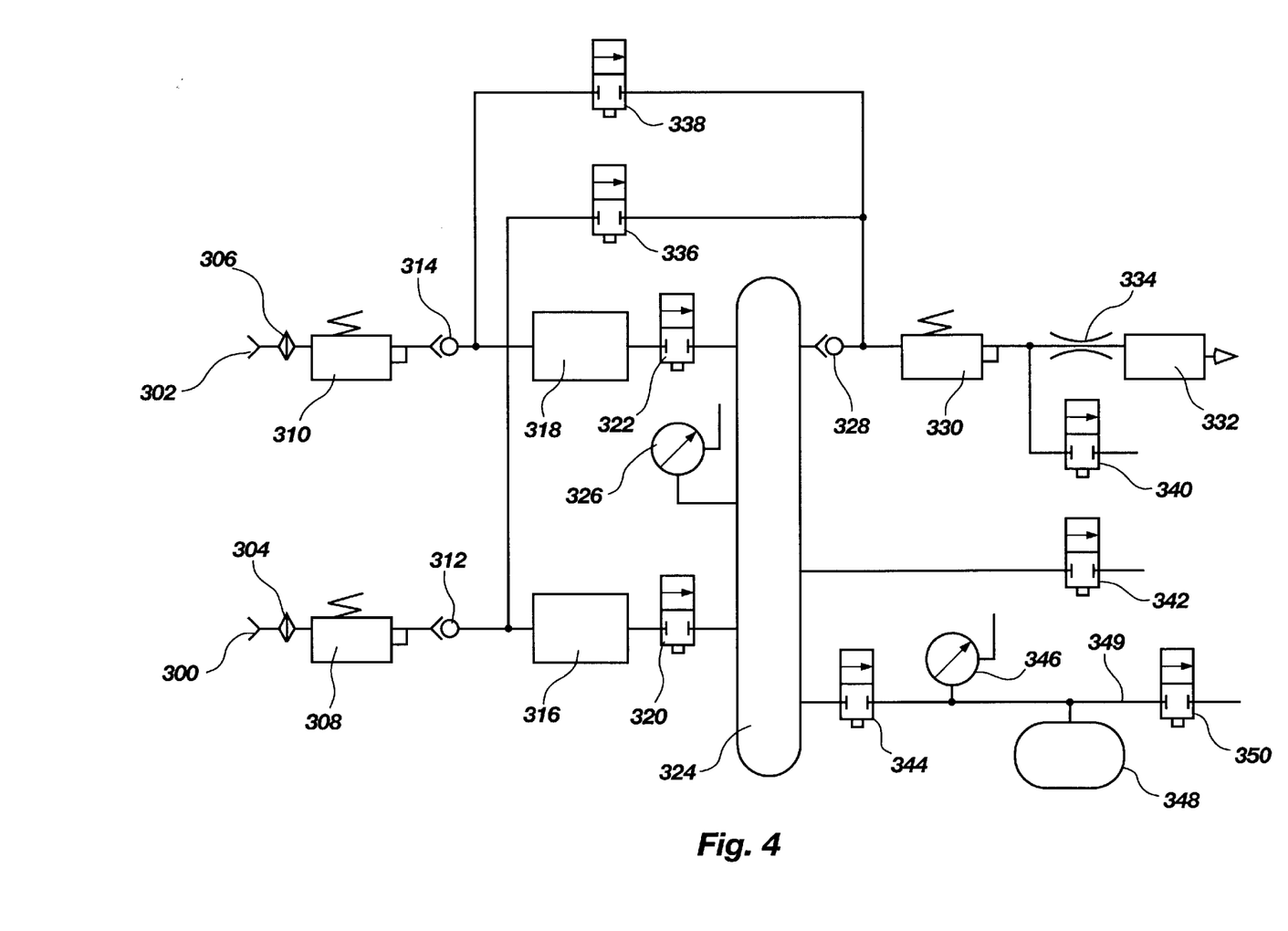
FIG. 4 is a schematic diagram of a gas blending and pressure regulator for use with the ventilator system of the present invention.

FIG. 4 is a pneumatic diagram of a gas blending and pressure regulator or mixer for use with the ventilator system. A source of compressed air 300 and oxygen 302 are connected to filters 304 and 306 respectively. Both gases are then regulated to some fixed pressure, for example 45 psig, by pressure regulators 308 and 310. Check valves 312 and 314 are used to prevent contamination of either source of compressed gas should the supply pressure of one drop below that set by the fixed regulators 308 and 310.

The flow rate of the regulated gases are each measured by mass flow meters 316 and 318. The mass flow meters are preferably of the type AWM5104 manufactured by Honeywell Microswitch, Freeport, Ill. The flow rate of each gas is controlled by a pair of proportional, 2 way solenoid valves 320 and 322 which may be of the type VSONC-6S25-VD-Q manufactured by Parker Pneutronics, Hollis, N.H. An electronic controller (not shown) adjusts the driving voltage to each of the proportional valves 320 and 322 to achieve a particular ratio of flows between the air and oxygen to arrive at the desired oxygen percentage once the outputs are combined. The absolute flow of each gas is confined by the mass flow meters 316 and 318; and the opening of the proportional valves 320 and 322 may be adjusted as necessary to attain the desired absolute flow. A reservoir 324 receives the output of each of the proportional valves 320 and 322 and allows the gases to mix. That is, the gases are transmitted to the reservoir with the input flow of each contributing to the mixing. The pressure within the reservoir 324 is measured using a pressure transducer 326 to ensure that sufficient blended gas is available to an associated ventilator system. As gas is drawn out of the reservoir 324, the pressure in the reservoir 324 drops and the electronic controller adjusts the output of both proportional valves 320 and 322 as required to maintain a particular pressure and blend ratio. This portion of the blender is similar in design to gas blenders used in a number of conventional ventilators.

A portion of the blended gas flows from the reservoir 324, through check valve 328 and is regulated to a lower pressure, for example 4.5 psig, by a fixed regulator 330. This low pressure blended gas is connected to an electrochemical oxygen sensor 332 similar to the Ceramatec 250, produced by Ceramatec, Salt Lake City, Utah. A fixed orifice flow restrictor 334 in the line limits the flow to a rate appropriate to the oxygen sensor 332.

To calibrate the oxygen sensor, a two way solenoid valve 336 is connected to the regulated source of compressed air and is opened to supply compressed air to the pressure regulator 330. The pressure of air exiting valve 336 will be greater than the pressure within the reservoir 324 so that check valve 328 will close and prevent dilution of the blended gas. The air flow through the valve 336 will be controlled by the pressure regulator 330 and the flow restrictor 324. Once air is present at the oxygen sensor, and the output voltage allowed to stabilize, a reading will be made and stored by the electronic controller. Next, valve 336 is closed and valve 338 is opened to expose the oxygen sensor 332 to 100% oxygen. A second reading will be made and a two point calibration accomplished by the electronic controller.

A second connection to the output of the low pressure regulator 330 is made to a two way solenoid valve 340. The output of valve 340 is used as a source of purge gas to maintain the airway pressure pathway in the nozzle as described previously.

Blended gas to be delivered to the patient is drawn from the reservoir 168 through an additional two way proportional valve 344. By monitoring the pressure downstream of valve 344 using a pressure transducer 346, the gas pressure in the line may be adjusted as required by the ventilator system. A reservoir 348 attached to the line 349 adds compliance and reduces the demands on the proportional valve 344 to meet substantially instantaneous changes in gas flow.

A large bore, two-way solenoid valve 350 is used as an isolation valve. Under normal use, this valve 350 is held open. Should the ventilator system detect a fault in any component which may lead to an excessive pressure or volume of gas to be delivered, this valve 350 may be closed to effectively isolate the patient. In this event, the patient may breath room air via the open end of the nozzle and/or corrugated tubing.

A final connection to the mixing reservoir 324 is made to a large bore 2 way solenoid valve 342. The output of valve 342 is available as an auxiliary blended gas supply for use with a float type flow meter and to supply a bag or mask for an ambulatory patient. The valve 342 is operated by the electronic controller on demand of the clinician using a fixed switch on the front panel of the device labeled hand bag.

Figure 5:
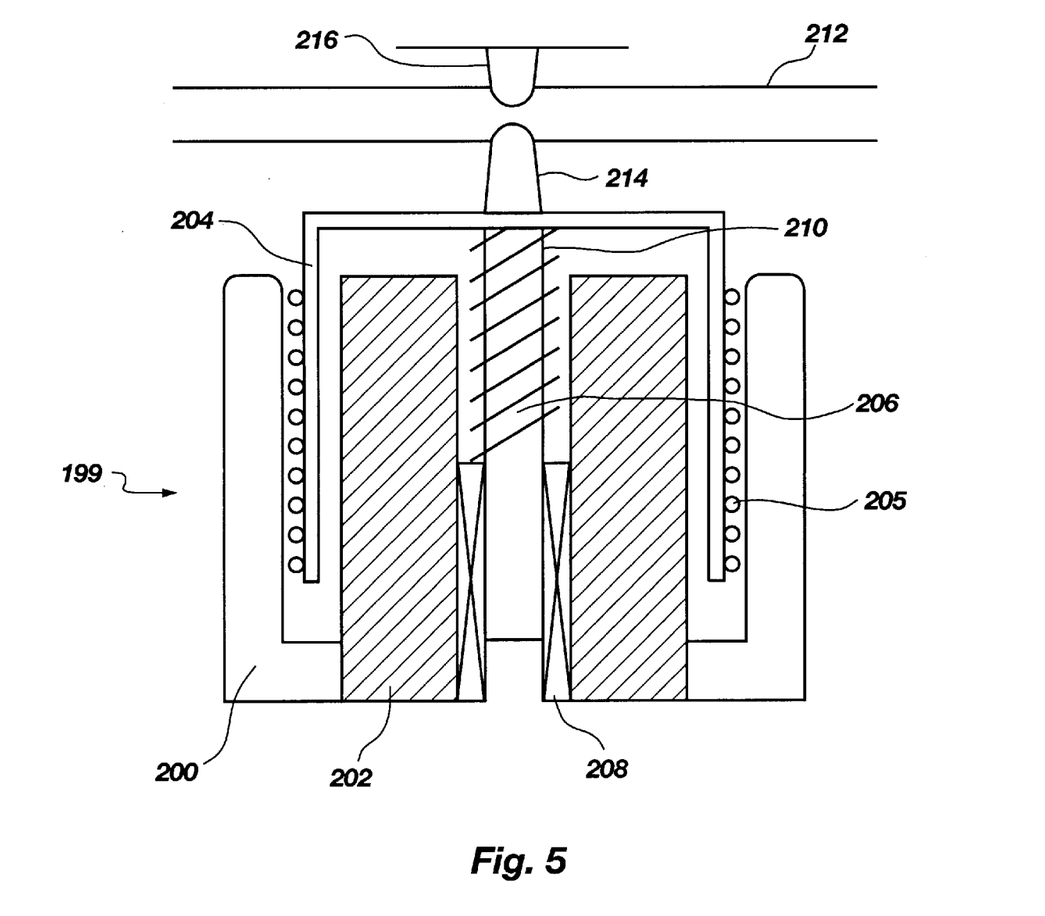
FIG. 5 is a schematic representation of a proportional valve for use with the ventilator system of the present invention.

FIG. 5 is a schematic representation of a variable position pinch valve 199 for use as the proportional inhalation valve of the ventilator system. The valve 199 uses a linear motor, also referred to as a moving coil motor similar to that found in loud speakers. The linear motor is composed of an electrical steel body 200 and a rare earth permanent magnet element 202. The moving coil 204 is fabricated using an aluminum or plastic bobbin and is wound with a number of turns of copper wire. The low mass of the moving coil structure 204 allows the device to have a very high frequency response which in this application minimizes the time required to respond to changes in gas flow demand. As power is applied to the coil, it is alternately attracted and repelled by the permanent magnet structure 200 and 202.

The moving coil 205 is supported by a non magnetic shaft 206 and linear bearing structure 208. A spring 210 urges the coil upwards and causes the lower pinch bar 214 to compress the compliant tubing 212 against the upper pinch bar 216. As a result, with no power applied, the valve 199 is normally closed. By careful design of the profile of the pinch bars 214 and 216 and selection of the compliant tubing 212, the spring forces required to close the tubing against the anticipated maximum gas driving pressure may be minimized. The illustrated configuration ultimately reduces the size and power required by the linear motor. When power is applied to the moving coil 205 in the appropriate polarity so as to cause the moving coil 205 to be attracted to the magnet structure 200 and 202, the lower pinch bar 214 is moved away from the upper pinch bar 216 because the housing 204 moves away from the tubing 212. In turn, gas flows through the compliant tube 212. The amount of power applied to the moving coil 204 will determine the degree of opening of the compliant tubing 214. If the polarity of the power applied to the moving coil 204 is reversed, the coil is urged away from the magnet structure 200 and 202 and the compliant tubing 212 more tightly pinched. This may be used to rapidly close the inhalation valve or to hold the valve closed against high gas pressures.

Figure 6:
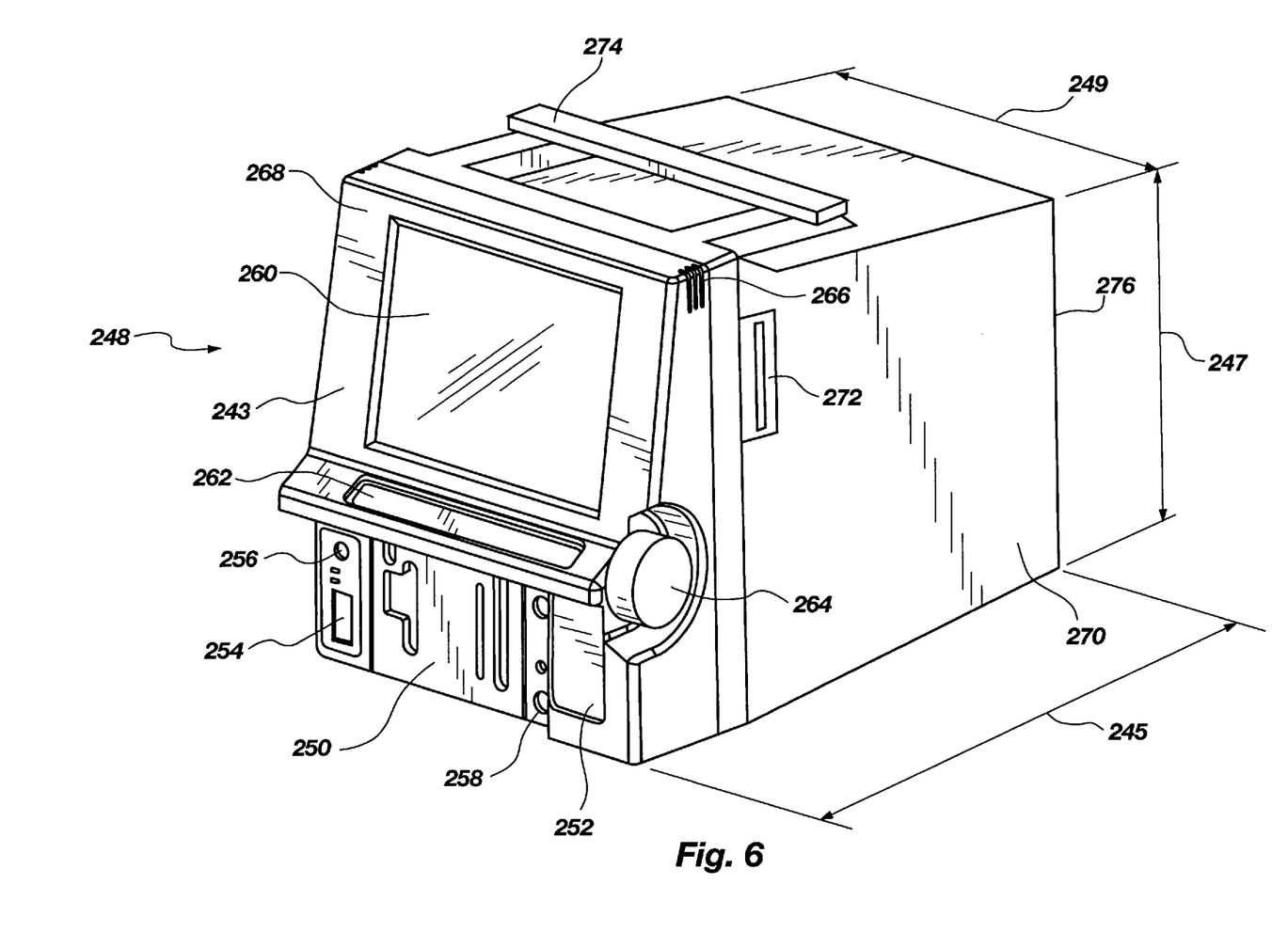
FIG. 6 is a chassis for use with a ventilator system of the present invention.

FIG. 6 is an example of a design for a chassis 248 suitable for the ventilator system of the current invention. The chassis 248 itself may be formed of sheet metal or molded from a suitable plastic material. Pressure forming of thermoplastic materials is one process that may be used to form the chassis 248. The internal system components would be supported on some form of metal support within that allows access for servicing. The chassis may measure no more than 14 inches in any direction 249, 245 and 247.

The external features of the chassis include the humidifier access door 250, and water pump 252. A power switch 254, blended gas outlet 256 and a connector 258 for a patient control module tether are also located on the lower portion of the front of the chassis 248. The upper portion of the front 243 of the chassis includes all of the user interface such as for example the touch screen 260 similar to touch screen 134 and display 170 (FIG. 3). The upper portion 243 includes the display 170 and touch screen 134 with the fixed controls 262 and the rotary knob 264. A number of lamps 266 embedded in the upper, outside corners of the device will serve as alarm indicators and would be visible from the sides of the chassis 248.

The chassis 248 includes a front bezel 268 and a rear cover 270. An opening in the rear cover 270 would allow access to a floppy disk drive 272 for entering new operating software or storage of patient and device performance records. A metal extrusion 274 along the top of the chassis 248 will serve as a carrying handle as well as an attachment point for various accessories including a shelf or brackets for other equipment like pulse oximeters or cardiac monitors.

Not shown is the rear of the enclosure 276 which includes the power entry, gas connections and communications ports. A door provides access to the internal batteries. The oxygen sensor would also be mounted to the rear panel to allow access by the user for convenient replacement as required.

Also not shown is the patient control module within a separate, much smaller chassis. The smaller chassis is sized and configured to be placed in the bed with the patient preferably proximate the patient's head. As a result it must be small, operate quietly, not generate excessive heat, have no rough surfaces or sharp edges and be able to withstand drops and repeated cleaning.

The use of a microprocessor, LCD display and touch-screen allows the user interface to be changed via software. The information presented or the format for this information may be readily changed.

In operation, the screen displays current operating parameters and controls as well as the airway pressure and flow waveforms. Another display accessible by the user via the touchscreens shows pulmonary function curves including pressure/volume or flow/volume loops.

The ventilator system described will be continuously monitoring the airway pressure and the flow of gas into and out of the patient. Additional physiologic information may be ported into the ventilator from other monitors and recorded. Such information may include pulse oximetry, exhaled carbon dioxide, heart rate, and blood pressures. All of such information may be stored and displayed as trending data to show the progress of the patient over time. Significant changes in operating parameters may also be displayed as part of this trending information. The stored information may also be transferred to a floppy disk or printed out for inclusion in the patient record.

Patient treatment protocols may be developed and included in the software of the ventilator so that the device may suggest or implement changes to the respiratory therapy in response to the condition of the patient. Information regarding adherence to or deviations from the established protocols for patient management may also be communicated to the user and recorded.

What is claimed is:

1. A ventilation system for supplying gas to a patient, said ventilation system comprising:

a first source for supplying a first gas;

a second source for supplying a second gas;

mixing means connected to said first source to receive said first gas therefrom and to said second source to receive said second gas therefrom, said mixing means having an outlet and said mixing means being operable for mixing said first gas and said second gas together into a gas mixture and being operable to supply one of said first gas, said second gas and said gas mixture at said outlet as a breathable gas;

processing means for heating and humidifying said breathable gas, said processing means being connectable to receive said breathable gas from said mixing means and to supply a processed gas;

a proportional valve connected to said processing means to receive said processed gas therefrom, said proportional valve being adapted to be positioned proximate a patient and said proportional valve being operable to regulate the pressure of the processed gas and to regulate the mode in which the processed gas is delivered to the patient;

a nozzle having an interior channel with a first end for connection to an endotracheal tube for positioning in the trachea of a patient and a second end opposite said first end, said nozzle having a first port for connection to receive said processed gas from said proportional valve and to supply said processed gas to said channel and a second port in communication with said channel to sense the pressure of gas in said channel;

exhaust means connected to said second end to exhaust gas from said patient, said exhaust means including a tube having an interior perimeter and a plurality of corrugations in which the corrugations have a minor dimension and a major dimension, said corrugations being sized to collect liquid-like materials from said exhaust gas, said tube further having a plurality of holes spaced apart about said perimeter proximate said minor dimension for the passage of gas from interior said exhaust means to exterior said exhaust means;

pressure sensing means connected to said second port for sensing the gas pressure in said channel and to supply a signal reflective of the gas pressure in said channel;

control means electrically connected to said pressure sensing means for receiving said signal reflective of the gas pressure in said channel, electrically connected to said mixing means to supply mixing signals thereto to cause said mixing means to supply said breathable gas and electrically connected to said proportional valve to supply operational signals thereto to select the pressure and the mode said processed gas is delivered to said nozzle;

input means associated with said control means for selecting a desired breathable gas and for selecting the pressure and the mode of processed gas to be delivered to said nozzle; and display means associated with said control means for displaying to a user symbols reflective of the gas pressure in said channel, symbols reflective of the breathable gas and symbols reflective of the pressure and mode of the processed gas delivered to said nozzle.

2. The ventilation system of claim 1 wherein said tube has a heater wire and wherein said heater wire is connectable to a source of electricity to supply electricity to said heater wire to cause said heater wire to generate heat.

3. The ventilation system of claim 2 further including a first purge line connected to receive said breathable gas, a purge valve connected to said purge line and operable between an open and a closed position, a sensing line connected between said pressure sensing means and said second port to supply a gas signal reflective of the pressure in said channel and a second purge line connected to said purge valve and interconnected into said pressure sensing line, and wherein control means is connected to said purge valve to supply operation signals thereto, and wherein said control means is operable to sense blockage of said second port and to thereupon cause said purge valve to move to its open position to supply breathable air through said first purge line and said second purge line to said port for purging said port.

4. The ventilation system of claim 3 wherein said purge valve is repetitively opened and closed until the blockage is no longer sensed.

5. The ventilation system of claim 4 wherein said control means is configured to cause said purge valve to be opened for a period of about 15 milliseconds.

6. The ventilation system of claim 5 wherein said control means includes a touch screen for the user to touch to select desired ventilation system parameters.

7. The ventilation system of claim 1 wherein said proportional valve is a servo controlled valve that is operable between a closed position and an open position and is configured to be normally closed and to fail closed.

8. The ventilation system of claim 1 wherein said mixing means includes a first inlet connected to receive said first gas from said first source, a first pressure regulator connected to receive said first gas from said first inlet, a first mass flow meter connected to said first pressure regulator to receive said first gas therefrom, a second inlet connected to receive said second gas from said second source, a second pressure regulator connected to receive said second gas from said second inlet, a second mass flow meter connected to said second pressure regulator to receive said second gas therefrom, and a reservoir connected to said first mass flow meter to receive said first gas therefrom and said second mass flow meter to receive said second gas therefrom, said reservoir being sized for mixing said first gas and said second gas to be said breathable gas.

9. The ventilation system of claim 8 wherein said mixing means further includes a first proportional valve connected to receive said first gas from said first pressure regulator and to said reservoir and to supply said first gas to said reservoir, and a second proportional valve connected to receive said second gas from said second pressure regulator, said first proportional valve and said second proportional valve each being connected to said control means to receive signals to operate said first proportional valve and said second proportional valve to supply the gas at a desired mixture.

10. The ventilation system of claim 9 wherein said mixing means includes an outlet having an oxygen sensor positioned therein to sense the amount of oxygen in said breathable gas and to said control means to supply signals reflective of the amount of oxygen is in said breathable gas.

11. The ventilation system of claim 10 wherein said proportional valve connected to said processing means is a solenoid controlled pinch valve.

12. A ventilation system for supplying gas to a patient, said ventilation system comprising:

a first source for supplying a first gas;

a second source for supplying a second gas;

mixing means connected to said first source to receive said first gas therefrom and to said second source to receive said second gas therefrom, said mixing means having an outlet and said mixing means being operable for mixing said first gas and said second gas together into a gas mixture and being operable to supply one of said first gas, said second gas and said gas mixture at said outlet as a breathable gas;

processing means for heating and humidifying said breathable gas, said processing means being connectable to receive said breathable gas from said mixing means and to supply a processed gas at a desired temperature and humidity;

a proportional valve connected to said processing means to receive said processed gas therefrom, said proportional valve being adapted for positioning proximate a patient and said proportional valve being operable to regulate the pressure of the processed gas and to regulate the mode in which the processed gas is delivered to the patient;

delivery conduit means connected to said processing means and to said proportional valve to communicating said breathable gas from said processing means to said proportional valve;

heater means positioned for heating the breathable gas in said delivery conduit;

a nozzle having an interior channel with a first end for connection to an endotracheal tube for positioning in the trachea of a patient and a second end opposite said first end, said nozzle having a first port for connection to receive said processed gas from said proportional valve and to supply said processed gas to said channel and a second port in communication with said channel to sense the pressure of gas in said channel;

exhaust means connected to said second end to exhaust gas from said patient, said exhaust means including a tube having an interior perimeter and a plurality of corrugations in which the corrugations have a minor dimension and a major dimension, said corrugations being sized to collect liquid-like materials from said exhaust gas, said tube further having a plurality of holes spaced apart about said perimeter proximate said minor dimension for the passage of gas from interior said exhaust means to exterior said exhaust means;

pressure sensing means connected to said second port for sensing the gas pressure in said channel and to supply a signal reflective of the gas pressure in said channel;

control means electrically connected to said pressure sensing means for receiving said signal reflective of the gas pressure in said channel, electrically connected to said mixing means to supply mixing signals thereto to cause said mixing means to supply said breathable gas and electrically connected to said proportional valve to supply operational signals thereto to select the pressure and the mode said processed gas is delivered to said nozzle;

input means associated with said control means for selecting a desired breathable gas and for selecting the pressure and the mode of processed gas to be delivered to said nozzle; and display means associated with said control means to a user symbols reflective of the gas pressure in said channel, symbols reflective of the breathable gas and symbols reflective of the pressure and mode of the processed gas delivered to said nozzle.

13. The ventilation system of claim 12 wherein said tube has a heater wire and wherein said heater wire is connectable to a source of electricity to supply electricity to said heater wire to cause said heater wire to generate heat.

14. The ventilation system of claim 12 further including a chassis configured to contain said control means and said processing means.

* * * * *